(12) United States Patent
Hesketh et al.

(10) Patent No.: US 8,067,198 B2
(45) Date of Patent: Nov. 29, 2011

(54) PROTEIN EXPRESSION SYSTEM

(75) Inventors: John Hesketh, Newcastle-Upon-Tyne (GB); Hanne Ravneberg, Bergen (NO); Christine Gjerdrum, Bergen (NO); Albert Tauler, Barcelona (ES); Ian Pryme, Bergen (NO); Beate Stern, Bergen (NO)

(73) Assignee: Prolume Ltd., Pine Top, AZ (US)

( * ) Notice: Subject to any disclaimer, the term of this patent is extended or adjusted under 35 U.S.C. 154(b) by 389 days.

(21) Appl. No.: 10/561,734

(22) PCT Filed: Jun. 25, 2004

(86) PCT No.: PCT/GB2004/002779
§ 371 (c)(1),
(2), (4) Date: Jun. 12, 2006

(87) PCT Pub. No.: WO2005/001099
PCT Pub. Date: Jan. 6, 2005

(65) Prior Publication Data
US 2007/0142623 A1    Jun. 21, 2007

Related U.S. Application Data

(60) Provisional application No. 60/499,146, filed on Aug. 29, 2003.

(30) Foreign Application Priority Data

Jun. 25, 2003 (GB) .................................. 0314856.6

(51) Int. Cl.
*C12N 15/00* (2006.01)
*C07K 14/00* (2006.01)
(52) U.S. Cl. ........................................ 435/69.1; 530/300
(58) Field of Classification Search .................. None
See application file for complete search history.

(56) References Cited

U.S. PATENT DOCUMENTS

| | | | |
|---|---|---|---|
| 5,876,995 A | 3/1999 | Bryan | 435/189 |
| 6,066,781 A | 5/2000 | Sutliff et al. | |
| 6,113,886 A | 9/2000 | Bryan | 424/49 |
| 6,152,358 A | 11/2000 | Bryan | 229/87.19 |
| 6,232,107 B1 | 5/2001 | Bryan et al. | 435/189 |
| 6,247,995 B1 | 6/2001 | Bryan | 446/473 |
| 6,416,960 B1 * | 7/2002 | Bryan | 435/7.23 |
| 6,436,682 B1 | 8/2002 | Bryan et al. | 435/189 |
| 2002/0004942 A1 | 1/2002 | Bryan | 800/288 |
| 2003/0066096 A1 | 4/2003 | Bryan | 800/8 |

FOREIGN PATENT DOCUMENTS

| | | |
|---|---|---|
| EP | 0 266 057 | 5/1988 |
| EP | 0 279 582 | 8/1988 |
| JP | 2001-258565 | 9/2001 |
| WO | WO 87/03300 | 6/1987 |
| WO | WO 91/13151 | 9/1991 |
| WO | WO 93/04165 | 3/1993 |
| WO | WO 97/29319 | 8/1997 |
| WO | WO 98/36081 | 8/1998 |
| WO | WO 98/36085 | 8/1998 |
| WO | WO 99/13090 | 3/1999 |
| WO | WO 99/49010 | 9/1999 |
| WO | WO 99/49019 | 9/1999 |
| WO | WO 00/26366 | 5/2000 |
| WO | WO 00/50616 | 8/2000 |
| WO | WO 02/46430 | 6/2002 |

OTHER PUBLICATIONS

Allet et al. (1997) Protein Expression and Purification, vol. 9, pp. 61-68.*
Brumell et al.,"SopD2 is a novel type III secreted effector of Salmonella typhimurium that targets late endocytic compartments upon delivery into host cells", Traffic 4: 36-48 (Jan. 2003).*
EBI Accession No. EM-PRO: U89490 (Sequence Listing).
EBI Accession No. UNIPROT: Q9BLZ2 (Sequence Listing).
Hesketh et al., "Intracellular Sorting of Macromolecules," Biochemical Society Transactions, vol. 24 No. 2 pp. 521-527, (1996).
Huang and Yen, "Hepatitis B Virus RNA Element That Facilitates Accumulation of Surface Gene Transcripts in the Cytoplasm," Journal of Virology, vol. 68, No. 5, pp. 3193-3199, (May 1994).
Inouye S. et al., "Imaging of luciferase secretion from transformed Chinese hamster ovary cells," Proc. Natl. Acad. Sci., vol. 89, pp. 9584-9587, (Oct. 1992).
Instruction Manual Entitled "pSecTag2/Hygro A, B, and C," Catalog No. V910-20.
Kim et al., "Molecular Cloning and Expression of Human Galβ1,3GalNAc α2,3-Sialytransferase (hST3Gal II)," Biochemical and Biophysical Research Communication, vol. 228, pp. 324-327, (1996).
Maeda et al., "Efficient Production of Active TNF-α by Albumin Signal Peptide," Biochemistry and Molecular Biology International, vol. 42, No. 4, pp. 825-832, (Jul. 1997).
Miesenböck and Rothman, "Patterns of synaptic activity in neural networks recorded by light emission from synaptolucins," Proc. Natl. Acad. Sci., vol. 94, pp. 3402-3407, (Apr. 1997).
Partridge et al., "Competition between the signal sequence and a 3'UTR localization signal during redirection of beta-globin mRNA to the endoplasmic reticulum: implications for biotechnology," Cytotechnology, vol. 30, pp. 37-47, (1999).
Thompson et al., "*Vargula hilgendorfii* luciferase: a secreted reporter enzyme for monitoring gene expression in mammalian cells," Gene, vol. 96:2, pp. 257-262, (1990).
Thompson et al., "Cloning and expression of cDNA for the luciferase from the marine ostracod *Vargula hilgendorfii*," Proc. Natl. Acad. Sci., vol. 86, pp. 6567-6571; (Sep. 1989).
Veyrune et al., "A localization signal in the 3' untranslated region of c-*myc* mRNA targets c-*myc* mRNA and β-globin reporter sequences to the perinuclear cytoplasm and cytoskeletal-bound polysomes," Journal of Cell Science, vol. 109, pp. 1185-1194, (1996).

(Continued)

*Primary Examiner* — Anand Desai
(74) *Attorney, Agent, or Firm* — Ballard Spahr LLP

(57) ABSTRACT

The present invention relates to a method of producing a target protein, which method comprises expressing said protein in a host cell which contains a nucleic acid molecule which encodes a chimeric protein, said chimeric protein comprising a signal peptide from a non-mammalian bulk-secreted protein and said target protein; nucleic acids, vectors, host cells and kits for carrying out the method are also described.

10 Claims, 8 Drawing Sheets

OTHER PUBLICATIONS

Zambetti et al., "Targeting of a chimeric human histone fusion mRNA to membrane-bound polysomes in HeLa cells," Proc. Natl. Acad. Sci., vol. 84, pp. 2683-2687, (May 1987).

Ahn, J.O., et al Over Expression of Thermoalkalophilic Lipase from *Bacillus stearothermophilus* L1 in *Saccharomyces cerevisiae*, J. Microbiol. Biotechnol. (2003) 13(3), 451-456.

International Search Report issued May 9, 2005 for PCT/GB2004/002779 filed on Jun. 25, 2004, which published on Jan. 6, 2005 as WO 2005/001099 (Hesketh et al. listed as inventors and Unitargeting Research AS listed as Applicant).

International Preliminary Report on Patentability and Written Opinion issued Jan. 3, 2006 for PCT/GB2004/002779 filed on Jun. 25, 2004, which published on Jan. 6, 2005 as WO 2005/001099 (Hesketh et al. listed as inventors and Unitargeting Research AS listed as Applicant).

Amatruda JF, Gattermeir DJ, Karpova TS, Cooper JA. (1992) Effects of null mutations and overexpression of capping protein on morphogenesis, actin distribution and polarized secn in yeast. J Cell Biol. 119(5): 1151-1162.

Erratt JA, Douglas PE, Moranelli F, Seligy VL. (1984) The induction of alpha-amylase by starch in *Aspergillus oryzae*: evidence for controlled mRNA expression. Can J Biochem Cell Biol. 62(8): 678-690.

Jennes W, Vereecken C, Fransen K, de Roo A, Kestens L. (2004) Disturbed secretory capacity for macrophage inflammatory protein (MIP)-1 alpha and MIP-1 beta in progressive HIV infection. AIDS Res Hum Retroviruses. 20(10): 1087-1091.

Kaneko M, Itoh H, Ueguchi-Tanaka M, Ashikari M, Matsuoka M. (2002) The alpha-amylase induction in endosperm during rice seed germination is caused by gibberellin synthesized in epithelium. Plant Physiol. 128(4): 1264-1270.

Kolarow R, Brigadski T, Lessmann V. (2007) Postsynaptic secretion of BDNF and NT-3 from hippocampal neurons depends on calcium calmodulin kinase II signaling and proceeds via delayed fusion pore opening. J Neurosci. 27(39): 10350-10364.

Lessmann V, Gottmann K, Malcangio M. (2003) Neurotrophin secretion: current facts and future prospects. Prog Neurobiol. 69(5): 341-374.

Liu G, Greenshields DL, Sammynaiken R, Hirji RN, Selvaraj G, Wei Y. (2007) Targeted alterations in iron homeostasis underlie plant defense responses. J Cell Sci. 120(Pt 4): 596-605.

Perrin D, Möller K, Hanke K, Söling HD. (1992) cAMP and Ca(2+)-mediated secretion in parotid acinar cells is associated with reversible changes in the organization of the cytoskeleton. J Cell Biol. 116(1): 127-134.

Kamiya T, Sugio S, Yamanouchi K, Kagitani Y. (1996) Secretion of active Fc fragments of immunoglobulin E directed by the yeast invertase signal sequence in mammalian cells. Tohoku J Exp Med. 180(4): 297-308.

Communication pursuant to Article 94(3) EPC issued Jun. 8, 2010 for EP Application No. 04 743 127.5-2405, which EP application claims priority to PCT/GB2004/002779 filed on Jun. 25, 2004 (Hesketh et al. listed as inventors and Prolume, Ltd. as Applicant).

Response to Communication filed Feb. 4, 2009 for EP Application No. 04 743 127.5-2405, which EP application claims priority to PCT/GB2004/002779 filed on Jun. 25, 2004 (Hesketh et al. listed as inventors and Prolume, Ltd. as Applicant).

Communication pursuant to Article 94(3) EPC issued Jul. 25, 2008 for EP Application No. 04 743 127.5-2405, which EP application claims priority to PCT/GB2004/002779 filed on Jun. 25, 2004 (Hesketh et al. listed as inventors and Prolume, Ltd. as Applicant).

Response to Communication filed Jan. 14, 2008 for EP Application No. 04 743 127.5-2405, which EP application claims priority to PCT/GB2004/002779 filed on Jun. 25, 2004 (Hesketh et al. listed as inventors and UniTargeting Research AS as Applicant).

Loss of Rights pursuant to R. 69(1) EPC issued on Nov. 2, 2007 for EP Application No. 04 743 127.5-2405, which EP application claims priority to PCT/GB2004/002779 filed on Jun. 25, 2004 (Hesketh et al. listed as inventors and UniTargeting Research AS as Applicant).

Communication pursuant to Article 96(2) EPC issued Mar. 15, 2007 for EP Application No. 04 743 127.5-2405, which EP application claims priority to PCT/GB2004/002779 filed on Jun. 25, 2004 (Hesketh et al. listed as inventors and UniTargeting Research AS as Applicant).

First Examination Report issued Nov. 27, 2009 for IN Application No. 388/DELNP/2006, which IN application claims priority to PCT/GB2004/002779 filed on Jun. 25, 2004 (Hesketh et al. listed as inventors and Prolume Limited as Applicant).

Response to First Examination Report filed Nov. 25, 2010 for IN Application No. 388/DELNP/2006, which IN application claims priority to PCT/GB2004/002779 filed on Jun. 25, 2004 (Hesketh et al. listed as inventors and Prolume Limited as Applicant).

Hearing Notice issued Dec. 29, 2010 for IN Application No. 388/DELNP/2006, which IN application claims priority to PCT/GB2004/002779 filed on Jun. 25, 2004 (Hesketh et al. listed as inventors and Prolume Limited as Applicant).

Examination Report issued May 11, 2010 for JP Application No. 2006-516484, which JP application claims priority to PCT/GB2004/002779 filed on Jun. 25, 2004 (Hesketh et al. listed as inventors and UniTargeting Research AS as Applicant).

Office Action for KR Application No. 1020057024711, which KR application claims priority to PCT/GB2004/002779 filed on Jun. 25, 2004 (Hesketh et al. listed as inventors and UniTargeting Research AS as Applicant).

* cited by examiner

| | |
|---|---|
| Chymotrypsin (ogen) : | MAFLWLLSCWALLGTTFG (SEQ ID NO:5) |
| Trypsin (ogen) 2 : | MNLLLILTFVAAAVA (SEQ ID NO:6) |
| Trypsin (ogen) A : | MNPLLILTFVAAALA (SEQ ID NO:7) |
| Amylase : | MKFFLLLFTIGFCWA (SEQ ID NO:8) |
| Gaussia luciferase : | MGVKVLFALICIAVAEA (SEQ ID NO:1) |
| Vargula luciferase : | MKIILSVILAYCVT (SEQ ID NO:2) |

Figure 1

SEQUENCE LISTING

```
<160> NUMBER OF SEQ ID NOS: 9

<210> SEQ ID NO 1
<211> LENGTH: 17
<212> TYPE: PRT
<213> ORGANISM: Gaussia princeps

<400> SEQUENCE: 1

Met Gly Val Lys Val Leu Phe Ala Leu Ile Cys Ile Ala Val Ala Glu
1               5                   10                  15

Ala

<210> SEQ ID NO 2
<211> LENGTH: 14
<212> TYPE: PRT
<213> ORGANISM: Vargula hilgendorfii

<400> SEQUENCE: 2

Met Lys Ile Ile Leu Ser Val Ile Leu Ala Tyr Cys Val Thr
1               5                   10

<210> SEQ ID NO 3
<211> LENGTH: 51
<212> TYPE: DNA
<213> ORGANISM: Gaussia princeps

<400> SEQUENCE: 3
atgggagtga aagttctttt tgcccttatt tgtattgctg tggccgaggc c          51

<210> SEQ ID NO 4
<211> LENGTH: 45
<212> TYPE: DNA
<213> ORGANISM: Vargula hilgendorfii

<400> SEQUENCE: 4
atgaagataa taattctgtc tgttatattg gcctactgtg tcacc                 45
```

```
<210> SEQ ID NO 5
<211> LENGTH: 18
<212> TYPE: PRT
<213> ORGANISM: Homo sapiens

<400> SEQUENCE: 5

Met Ala Phe Leu Trp Leu Leu Ser Cys Trp Ala Leu Leu Gly Thr Thr
1               5                   10                  15

Phe Gly

<210> SEQ ID NO 6
<211> LENGTH: 15
<212> TYPE: PRT
<213> ORGANISM: Homo sapiens

<400> SEQUENCE: 6

Met Asn Leu Leu Leu Ile Leu Thr Phe Val Ala Ala Val Ala
1               5                   10                  15

<210> SEQ ID NO 7
<211> LENGTH: 15
<212> TYPE: PRT
<213> ORGANISM: Homo sapiens

<400> SEQUENCE: 7

Met Asn Pro Leu Leu Ile Leu Thr Phe Val Ala Ala Leu Ala
1               5                   10                  15

<210> SEQ ID NO 8
<211> LENGTH: 15
<212> TYPE: PRT
<213> ORGANISM: Homo sapiens

<400> SEQUENCE: 8

Met Lys Phe Phe Leu Leu Leu Phe Thr Ile Gly Phe Cys Trp Ala
1               5                   10                  15

<210> SEQ ID NO 9
<211> LENGTH: 6
<212> TYPE: PRT
<213> ORGANISM: Gaussia princeps

<400> SEQUENCE: 9

Ala Leu Ile Cys Ile Ala
1               5
```

PROTEIN EXPRESSION SYSTEM

CROSS REFERENCE TO RELATED APPLICATIONS

The present application claims priority to Great Britain Patent Application No 0314856.6, filed Jun. 25, 2003 and to U.S. Application No. 60/499,146, filed Aug. 29, 2003, which applications are incorporated herein fully by this reference.

The present invention relates to cell based expression systems and the expression and secretion of both naturally non-secreted and naturally secreted proteins through exploitation of genetic sequences from a particular class of proteins.

In the wake of the sequencing of the human genome, science has become increasingly aware of the role proteins play in disease. Protein based pharmaceuticals are becoming increasingly popular and their use requires large amounts of exceptionally pure protein.

Scientists are now beginning to map the proteome and the experiments involved are likely to warrant the availability of large amounts of highly purified protein. As our understanding of the roles proteins play in disease increases there will also be a need for diagnostic kits. Such kits may utilize purified proteins.

Prior to the advent of molecular biology a pure sample of protein could be only obtained by purification from a natural source. Proteins obtained in this fashion are never fully pure nor can large amounts be obtained. In addition there was always the risk of inclusion of pathogens/toxins from the natural source. Developments in recombinant technology have meant that proteins can be cloned and overexpressed in vitro. Commonly bacterial cells are used as the host expression system, although more recently, mammalian cells have also been used.

The correct physiological function of a mammalian protein is often dependent on its three dimensional structure and its post-translational modification (a signature of lipid or sugar modification unique to each protein and often unique to the species). Prokaryotic cells do not modify proteins in this way and so there is always doubt that a recombinant protein expressed in a prokaryotic cell will have the correct modification and fold and thus have full and true physiological activity. Furthermore there are concerns regarding contamination of the recombinant proteins with prokaryotic proteins from the host cells. This, of course, is of particular importance in the use of recombinant proteins in the clinical setting.

As such mammalian cell based systems are in demand. However, mammalian cells have the drawback of poor yield since their capacity for overexpression is significantly lower than prokaryotic cells. To address this the traditional approach has been to scale up the system and to harvest the product from vast amounts of cells. This poses obvious practical and economic problems. In addition previous approaches have sought to optimize the culture conditions to ensure maximum production from the cells.

As a general rule proteins that are naturally secreted from the cell are more straightforward to produce in cell factories because the recombinant protein is also secreted by the host. Thus the media can be removed and the recombinant protein purified to homogeneity. This of course leaves the cell factories to continue to produce more recombinant proteins. Problems are apparent if the recombinant protein is a non-secreted protein. In this case the cell factories must be sacrificed each time a harvest is made to enable the recombinant protein to be released from the cells. In addition the cell factory can only house so much intracellular recombinant protein before protein synthesis is attenuated to protect the integrity of the cell.

The present invention addresses these problems. By exploiting genetic signals that determine the post-translational fate of the nascent forms of a particular class of protein and the protein secretion machinery of host cells, the present invention both enhances the secretion of a protein which is normally secreted and induces the secretion of a protein which is normally non-secreted. This, therefore, improves the yield of secreted proteins and improves the efficiency of production and yield of non-secreted proteins.

All proteins destined for secretion by eukaryotic cells must pass through, in turn, the endoplasmic reticulum (ER) and the Golgi apparatus before being packaged into membrane bound vesicles that allow secretion. Secretion can be constitutive, regulated at the level of gene expression or regulated at the site of release.

The translation of mRNA occurs on ribosomes and ribosomes are only located in the cytoplasm. As such, the newly synthesized polypeptide chain of a secreted protein must enter the ER to enable it to be secreted. In 1975 Blobel and Dobberstain proposed the "signal hypothesis" whereby a stretch of peptides at the N-terminal end of secreted proteins promote the passage of a nascent polypeptide chain into the ER. The newly synthesized signal sequence is recognized by complexes in the ER membrane known as signal recognition particles (SRP's). Upon binding to an SRP the translation of the polypeptide is halted until the ribosome translating the mRNA attaches to the ER (Gorlich and Rapoport, 1993). Upon docking translation continues until a full length polypeptide is detached into the lumen of the ER.

This polypeptide then passes through the ER and the Golgi apparatus by which time it is correctly folded and post-translationaly modified. The unique chemical make up of the ER lumen and the presence of unique enzymes ensure the fidelity of this process. In the Golgi apparatus the proteins are packaged into membrane bound vesicles that will allow for constitutive secretion or regulated release according to the physiological role of the secreted protein.

Signal sequences from different proteins and different species display large variation in their actual sequence although common features are shared. There is a positively charged N-terminal region (n-region), a hydrophobic central region (h-region) and a slightly polar C-terminal region (c-region). The total length of the signal peptide is usually between 15 and 30 amino acids, although signal peptides of 50 residues have been documented. Variation occurs primarily in the n- and h-regions with the c-region being relatively constant (Martoglio and Dobberstein, 1998).

The n-region consists of about 2-5 amino acids and typically has a net charge of +2. The positive charge in the n-region is the result of the presence of basic residues. The central region is the h-region. A hydrophobic stretch usually of between 7 and 15 residues in an α-helical configuration (von Heijne, 2002). Unlike the n-region, disruption of this hydrophobic region through deletion or insertion on non-hydrophobic residues often leads to total loss of function. Disruption of the α-helical configuration also has a large impact on function (von Heijne 1990). The c-region follows the h-region and is approximately 5 residues in length and has a high frequency of proline and polar residues. This region is important for cleavage of the signal peptide from the polypeptide (Martoglio and Dobberstein, 1998).

The rough endoplasmic reticulum (RER) is well known to consist of a variety of subdomains. Three have been described: light rough (LR), heavy rough (HR) and nuclear-associated ER (NER) (Pryme, 1986; 1989a, b). These subdomains display differing characteristics. For instance, differences have been observed in the physical properties of the polysomes attached to them, the particular mRNA species contained in them, the post-translational modifications occurring within them (Pryme 1988), and also the physical character of the membranes that make up the sub-domains (Pryme and Hesketh, 1987 and Maltseva, et al, 1991). Targeting to these subdomains may involve the signal peptide.

As mentioned above secretion of proteins can be constitutive or regulated at the level of gene expression or at the point of release. Constitutive secretion occurs when a cell expresses a protein at a fixed rate and that protein passes through the secretion machinery of the cell to be released into the extracellular space without the cell exerting any particular control. Examples would include the extracellular matrix proteins and serum proteins such as albumin.

Secretion can be controlled at the level of gene expression. In this case stimuli cause the up- or down-regulation of the expression of the protein; however any protein that is expressed, once it enters the secretory pathway, will exit the cell in a largely unregulated manner. Examples would include release of hormones into the bloodstream (i.e. gastrin in response to food in the stomach and secretin in response to acid in the duodenum and jejunum).

Alternatively secretion, at the level of release, may be induced in response to extracellular stimulation. Examples include release of neurotransmitters from neurons into synapses, release of inflammatory mediators in response to other such mediators, release of gastric juices in response to cholecytokinin and release of dyes by marine invertebrates in response to tactile stimulation.

Regulation of release is achieved by packaging the protein to be secreted into vesicles that only fuse with the plasma membrane when a certain signal is received. Until that time these vesicles mass below the plasma membrane until the signal is received. These vesicles have high concentrations of secreted proteins whereas constitutive secretory vesicles often have much lower concentrations. The signal in the case of a neuron is an influx of $Ca^{2+}$ in response to an action potential. Upon receipt of such a signal the vesicular contents are released as one and the protein is "bulk-secreted".

Marine organisms, such as *Gaussia princeps* and *Vargula hilgendorfii*, in response to tactile stimulation release in bulk enzymes that can cause light emission from a co-released substrate. *Gaussia princeps* is found in deep, cold water. In contrast *Vargula hilgendorfi* is found in shallow warm water. Gaussia luciferase is approx 19K, 185 residues and has no glycosylation sites whereas Vargula luciferase is approximately 68K, 555 residues and has 7 O-glycosylation sites and 2 N-glycosylation sites.

Previous work has shown that the nucleotide sequence coding for the signal peptide derived from a constitutively secreted protein (albumin), when fused to the coding region of an mRNA of an exogenous protein, caused retargeting of the mRNA to membrane-bound polysomes associated with the ER (Partridge et al. 1999, WO 99/13090). This is a prerequisite for promoting secretion of the encoded protein. Also used to achieve secretion of recombinant proteins have been signal peptides from proteins whose secretion is regulated at the level of expression, (WO91/13151; Invitrogen vector pSecTag/Hygro A, B, C cat no V910-20; Kim 1996; EP 0279582; EP 0266057). WO 91/13151 and EP 0279582 involve genetic constructs stably integrated into the genome of transgenic animals and the secretion of exogenous proteins into the milk of that animal.

The signal peptide from human (WO 02/46430) and bovine (EP 0266057) growth hormone, a bulk-secreted protein, has been used to secrete recombinant proteins in mammalian cells. However, these signal peptides were not selected because of the bulk-secreted nature of growth hormone. WO 00/50616 discloses the use of a signal peptide from a mammalian bulk-secreted protein (human granulocyte macrophage colony stimulating factor, GMCSF) although this signal sequence was only shown to function if the entire GMCSF sequence was also used in addition to the signal peptide. Again, this signal peptide was not selected because of the bulk-secreted nature of GMCSF.

It has now been found that the signal peptides from bulk-secreted proteins when fused to either naturally secreted or naturally non-secreted proteins enhance the secretion of naturally secreted proteins or induce the secretion of naturally non-secreted proteins to a surprisingly high level.

Thus, in one aspect the present invention provides a method of producing a target protein, which method comprises expressing said protein in a host cell which contains a nucleic acid molecule which encodes a chimeric protein, said chimeric protein comprising a signal peptide from a non-mammalian bulk-secreted protein and said target protein. In other words, the chimeric protein comprises a signal peptide whose sequence is the same as, or is derived from, the signal peptide of a non-mammalian bulk-secreted protein.

The host cell can be obtained from any biological source. The host cell may be prokaryotic or eukaryotic, preferably eukaryotic. Of eukaryotic host cells fungal, plant, nematode, insect, crustacean, piscine, amphibian, reptilian, avian and mammalian cells are preferred. Most preferably the host cell is a mammalian host cell.

The encoded protein is a chimeric protein, i.e. the signal peptide is not the native signal peptide for the target protein. A chimeric polypeptide comprises two or more component sequences derived from two or more different molecules, preferably two sequences each derived from a different molecule.

Bulk-secreted proteins have signal peptides which target the nascent polypeptide to the RER and induce its translocation into the RER. The signal peptide also appears to contain information that directs the protein into secretory vesicles that are involved in regulated secretion, perhaps by targeting the nascent polypeptide to a particular ER subdomain. These vesicles are known to be able to package their contents at concentrations higher than vesicles involved in constitutive secretion. However, since the polypeptide fused to the signal peptide is not normally secreted, or not secreted in the same way, then the endogenous peptide is constitutively secreted at high levels instead.

The term "bulk-secreted protein" refers to a protein which, in its normal physiological environment, is packaged into vesicles which only fuse with the plasma membrane to release their contents in response to transient stimulus. In other words, proteins where the level of secretion is regulated at the post-translational level.

Thus, a signal peptide from a bulk-secreted protein is a sequence of amino acids, normally between about 15 and about 30 residues in length and normally found at the N-terminus of the protein which directs the nascent polypeptide chain to the ER and promotes its translocation into the ER lumen thus enabling the protein to enter the secretory pathway and become packaged into secretory vesicles that release their contents, typically in response to a transient stimulus. As demonstrated by the Examples herein, in the methods of the present invention an external transient stimulus is not necessarily required in order to prompt secretion of the target protein.

Encompassed within the term "signal peptide from a bulk-secreted protein" are fragments and/or derivates of naturally occurring sequences (in isolation or included within other sequences) which retain the ability to enhance or induce secretion of a target protein. Methods of testing the ability of peptides to act in this way are described in the Examples. In particular signal sequences which have either or both of their n-region and c-region deleted in part or in full are considered to be encompassed by the present invention. Fragments of naturally occurring sequences, or derivatives thereof, will typically have at least 6 amino acids, preferably at least 8 amino acids, more preferably at least 10 amino acids.

It is envisaged that derivatives of naturally occurring signal peptides from bulk-secreted proteins will have at least 40%, preferably 50 or 60% or more, particularly 70 or 80% or more sequence homology with the native sequence. For the purposes of the present invention "sequence homology" is not used to refer only to sequence identity but also to the use of amino acids that are interchangeable on the basis of similar physical characteristics such as charge and polarity. Substitution of an amino acid within a signal sequence with an amino acid from the same physical group is considered a conservative substitution and would not be expected to alter the activity of the signal peptide. Thus a derivative which just replaced leucine with isoleucine throughout would be considered to have 100% "sequence homology" with the starting sequence. Convenient groups are, glycine and alanine; serine, threonine, asparagine, glutamine and cysteine; lysine arginine and histidine; glutamic acid and aspartic acid; valine, leucine, isoleucine, methionine, phenylalanine, tryptophan and tyrosine. Preferred sub-groups within this last group include leucine, valine and isoleucine; phenylalanine, tryptophan and tyrosine; methionine and leucine. Sequence homology may be calculated as for 'sequence identity' discussed below but allowing for conservative substitutions as discussed above.

Preferably, the derivatives of naturally occurring signal peptides from bulk-secreted proteins (e.g. *Gaussia* luciferase, discussed in more detail below) exhibit at least 60%, preferably at least 70% or 80%, e.g. at least 90% sequence identity to a naturally occurring signal sequence or portion thereof (as determined by, e.g. using the SWISS-PROT protein sequence databank using FASTA pep-cmp with a variable pamfactor, and gap creation penalty set at 12.0 and gap extension penalty set at 4.0, and a window of 2 amino acids.

Techniques are well known in the art for preparing derivatives of a known starting sequence; nucleic acid molecules encoding functionally-equivalent (or improved) signal peptides may be produced by chemical synthesis or utilizing recombinant technology.

It is also envisaged that in a preferred embodiment of the invention the signal peptide fused to the target protein will be devoid of all or the majority of the native protein secreted by the signal peptide. Preferably less than 15 amino acid residues of the native protein will be present. Most preferably none of the native protein will be present. Thus the chimeric protein will preferably include in addition to the signal peptide itself, less than 15 amino acid residues of the native protein of the signal peptide and most preferably the chimeric protein will include none of the native protein of the signal peptide.

In another preferred embodiment of the invention the biological source of the signal peptide will not be the same as the biological source of the host cell, i.e. the signal peptide is heterologous for the host cell. Most preferably the signal peptide will be from a non-mammalian protein and the host cell will be a mammalian host cell.

The signal sequence may also be non linear. In other words fragments and/or derivates are distributed within the coding sequence of the target protein in a manner in which the activity of the signal peptide is still retained. Such fragments and/or derivates are therefore considered to fall within the present invention.

The invention utilizes signal peptides from bulk-secreted proteins. Preferred are signal peptides from a copepod or an ostracod, e.g. *Gaussia princess* or *Vargula hilgendorfii*. Particularly preferred are the signal peptides from *Gaussia* (MGVKVLFALICIAVAEA; SEQ ID No. 1) or *Vargula* (MKIILSVILAYCVT; SEQ ID No. 2) *luciferase* and most particularly the signal peptide from *Gaussia luciferase*.

Thus, in a preferred embodiment the invention provides a method of producing a target protein, which method comprises expressing said protein in a host cell which contains a nucleic acid molecule which encodes a chimeric protein, said chimeric protein comprising the signal peptide from *Gaussia luciferase* or a fragment or derivative thereof and said target protein. Preferred derivatives and suitable fragments are discussed above and below.

Preferred fragments will have at least 8 amino acids, typically at least 10 amino acids, e.g. at least 12 amino acids.

The sequence of the signal peptide from *Gaussia luciferase* is shown in FIG. 1 alongside those for Chymotrypsin (ogen), Trypsin (ogen) 2, trypsin (ogen) A, Amylase and Vargula luciferase (other bulk-secreted proteins). As can be seen the signal sequence for *Gaussia luciferase* has a unique motif: ALICIA (SEQ ID NO:9). Signal peptides which incorporate this sequence and variants and fragments of it are particularly preferred, e.g. fragments of 4-5 amino acids, and peptides incorporating conservative substitutions as discussed above.

Thus, in preferred embodiment the present invention provides a method of producing a target protein, which method comprises expressing said protein in a host cell which contains a nucleic acid molecule which encodes a chimeric protein, said chimeric protein comprising a signal peptide which includes the sequence ALICIA (SEQ ID NO:9) or a variant or fragment thereof and said target protein. Most preferably the ALICIA (SEQ ID NO:9) sequence is found in the h-region of the signal peptide. The signal peptide of such chimeric molecules will typically consist of 5 to 25 amino acids, preferable 5 to 20 amino acids, e.g. 8 to 18 amino acids.

The term "target protein" refers to the protein that is to be expressed and secreted according to the invention. Such proteins may include proteins not found in the host cell, proteins from different species or cloned versions of proteins found in the host cell. Preferred target proteins of the invention will be mammalian proteins, especially those that have complex folding, coenzyme groups, quaternary structure and/or require modifications to occur at any time during the expression of the protein from its coding sequence. Such modification may include modification of DNA encoding the protein (such as methylation or acetylation), modification of the RNA transcribed from the coding DNA (such as splicing, 5' capping) or modification of the nascent protein (such as glycosylation or lipid modification). It will be appreciated that only certain host cell types will be suitable for some types of modification.

Non-limiting examples of particularly preferred target proteins includes human tryptophan hydroxylase, G-protein coupled receptors and nuclear receptors.

Further non-limiting classes of target proteins include biopharmaceutical proteins (e.g. protein-replacement therapy in single-gene deficiency diseases e.g. Pompe's disease), proteins for which current manufacturing processes cannot guarantee high enough product quality and safety, proteins required in drug-design studies, biocatalysts and biosensors.

Target proteins may include both naturally non-secreted proteins and naturally secreted proteins. The term "non-secreted protein" refers to proteins whose normal environment is inside of or associated with the plasma membrane of a cell. Such proteins may be soluble or anchored to membranous structures.

The method of the invention can be used to enhance the secretion of naturally secreted proteins or to induce the secretion of naturally non-secreted proteins.

Thus, in a preferred embodiment the present invention provides a method of enhancing the secretion of a target protein which is naturally secreted, which method comprises expressing said protein in a host cell which contains a nucleic acid molecule which encodes a chimeric protein, said chimeric protein comprising a signal peptide from a non-mammalian bulk-secreted protein and said target protein.

In another preferred embodiment the present invention provides a method of inducing the secretion of a target protein which is not naturally secreted, which method comprises expressing said protein in a host cell which contains a nucleic acid molecule which encodes a chimeric protein, said chimeric protein comprising a signal peptide from a non-mammalian bulk-secreted protein and said target protein.

The term "nucleic acid molecule" refers to nucleic acid molecules consisting of any type of nucleic acid or modification or derivates thereof in single, double or other stranded form. Such nucleic acids include DNA, RNA, methylated DNA, acetylated DNA, nucleic acids containing artificial bases, etc. In the host cell, the nucleic acid encoding the chimeric proteins discussed above may be incorporated into the genetic material of that host cell.

A further aspect of the invention provides a nucleic acid molecule comprising a coding sequence for a signal peptide from a non-mammalian bulk-secreted protein operably linked to a coding sequence of a target protein, wherein the signal peptide is not the native signal peptide for the target protein, and sequences complementary and/or capable of hybridizing thereto under conditions of high stringency.

Alternatively viewed, in a further aspect the present invention provides a nucleic acid molecule encoding a chimeric protein which comprises a signal peptide from a non-mammalian bulk-secreted protein and a target protein.

Preferred nucleic acid molecules are those which include a region which encodes SEQ ID No. 1, the signal peptide of *Gaussia luciferase*, or variants or fragments thereof. Such active peptide variants and fragments are discussed above. The degeneracy of the genetic code means there are a class of molecules which are capable of encoding SEQ ID No. 1 (or SEQ ID No. 2, the signal peptide of *Vargula luciferase*). A class of preferred nucleic acid molecules will be those which incorporate a region (encoding a signal peptide) which:
 (a) is capable of hybridizing to one or more of the sequences which encode SEQ ID No. 1 or 2 under non-stringent binding conditions of 6×SSC/50% formamide at room temperature and washing under conditions of high stringency, e.g. 2×SSC, 65° C., where SSC=0.15 M NaCl, 0.015 M sodium citrate, pH 7.2; and/or
 (b) exhibits at least 70%, preferably at least 80, 90 or 95% sequence identity with one or more of the sequences which encode SEQ ID No. 1 or 2 or a portion thereof (as determined by, e.g. FASTA Search using GCG packages, with default values and a variable pamfactor, and gap creation penalty set at 12.0 and gap extension penalty set at 4.0 with a window of 6 nucleotides,
or a sequence complementary to any such sequence.

The nucleotide sequence of the *Gaussia* signal peptide is:

ATGGGAGTGAAAGTTCTTTTTGCCCTTATTTGTAT (SEQ ID No. 3)
TGCTGTGGCCGAGGCC;

and for the *Vargula* signal peptide is:
 ATGAAGATAATAATTCTGTCTGTTATAT-TGGCCTACTGTGTCACC; (SEQ ID No. 4). Thus a particularly preferred group of nucleic acid molecules according to the present invention and for use in the methods of the present invention are those which incorporate a region which:
 (a) is capable of hybridizing to SEQ ID No. 3 or 4 (preferably SEQ ID No. 3) under non-stringent binding conditions of 6×SSC/50% formamide at room temperature and washing under conditions of high stringency, e.g. 2×SSC, 65° C., where SSC=0.15 M NaCl, 0.015 M sodium citrate, pH 7.2; and/or
 (b) exhibits at least 70%, preferably at least 80, 90 or 95% sequence identity with SEQ ID No. 3 or 4 (preferably SEQ ID No. 3) or a portion thereof (as determined by, e.g. FASTA Search using GCG packages, with default values and a variable pamfactor, and gap creation penalty set at 12.0 and gap extension penalty set at 4.0 with a window of 6 nucleotides),
or a sequence complementary to any such sequence.

A further preferred group of nucleic acid molecules are those which incorporate a region which encodes an amino acid sequence which exhibits at least 70%, preferably at least 80, 90 or 95% sequence identity with SEQ ID No. 1 or 2 (preferably SEQ ID No. 1) or a portion thereof (as determined by, e.g. using the SWISS-PROT protein sequence databank using FASTA pep-cmp with a variable pamfactor, and gap creation penalty set at 12.0 and gap extension penalty set at 4.0, and a window of 2 amino acids.

The term "coding sequence" refers to the sequence of a nucleic acid molecule which is translatable. Such sequences will not contain introns or other untranslated sequences nor will any native signal sequence be present. The coding sequences may vary within the limits of the degeneracy of the standard genetic code and also with respect to conservative substitutions with non-standard bases.

The nucleic acid molecule may also comprise other sequences including origins of replication, selectable markers, transcriptional start sites, transcriptional enhancers, transcriptional inducers, transcriptional control elements, 3' untranslated control sequences, 5' untranslated control sequences, sequences to allow for detection and/or purification of the target protein product and sequences that allow for cloning, especially seamless cloning. The choice of the particular additional sequences will be dependent on the host cell type.

Polypeptides comprising a sequence encoded by any of the nucleic acid molecules defined above constitute a further aspect of the invention.

The term "seamless cloning" refers to cloning techniques whereby a resulting nucleic acid construct is formed in which no linker sequences exist in the translated region. Seamless cloning techniques include the Seamless® Cloning Kit from Stratagene Calif. USA, cat no. 214400 and the cloning technique disclosed in Example 1.

The term "linker sequences" refers to the sequences that remain after restriction digestion of nucleic acid by restriction enzymes which cleave within their recognition sites.

Another aspect of the invention is a vector comprising at least the sequence of a signal peptide from a non-mammalian bulk-secreted protein upstream from a cloning site in which the coding sequence of a target protein can be inserted resulting in an expression product of said vector which is a chimeric protein, said chimeric protein comprising a signal peptide from a non-mammalian bulk-secreted protein and said target protein. Such vectors incorporating sequences which encode target proteins are a further aspect of the invention.

The most preferred cloning technique is a seamless cloning technique and thus, in a preferred embodiment said cloning site is suitable for use in a seamless cloning technique.

In another preferred embodiment the invention provides a vector further comprising at least one from the following list in positions that allow for the true functioning of the sequence; an origin of replication, a selectable marker, a transcriptional start site, a transcriptional enhancer, a transcriptional inducer, a transcriptional control element, a 3' untranslated control sequence, a 5' untranslated control sequence and sequences to allow for detection and/or purification of the target protein product. The choice of the particular additional sequences will be dependent on the host cell type.

In an further aspect the invention provides a kit comprising a vector as defined above and optionally an engineered host cell line.

Expression of the target protein occurs in host cells and thus in a further aspect the invention provides a cell containing a nucleic acid molecule which encodes a chimeric protein, said nucleic acid molecule and said chimeric protein being defined and described above. The preferred types of host cells have been described previously. As stated the most preferred host cell is a mammalian host cell. The preparation of the nucleic acid construct of the invention may involve the use of intermediate (possibly non-mammalian) cells as hosts and these constitute a further embodiment of this aspect of the invention.

Preferably the host cell will be in culture and even more preferably the host cell will be in stable cell culture. Thus in a preferred embodiment the invention provides a cell in vitro containing a nucleic acid molecule which encodes a chimeric protein, said nucleic acid molecule and said chimeric protein being defined and described above, wherein said nucleic acid molecule is preferably stably transfected, even more preferably stably integrated into the genome of said cell. Thus, preferably, the methods of the invention are in vitro methods.

In a further aspect the invention provides a method for obtaining a target protein from the media of host cell cultures, said host cells containing a nucleic acid molecule encoding a chimeric protein, said nucleic acid molecule and said chimeric protein being defined and described above, which method comprises expressing said chimeric protein, harvesting the culture media of said cells and extracting and purifying said target protein therefrom. Methods of protein extraction and purification are well known in the art. Generally the signal peptide will be cleaved within the host cell and the secreted protein will be the target protein free, or substantially free, of signal peptide.

In a further aspect the invention provides a chimeric polypeptide comprising a signal peptide from a non-mammalian bulk-secreted protein fused to a heterologous protein of interest. Optionally the polypeptide also comprises peptide sequences to allow for its detection and/or purification.

In a further aspect the invention provides a method of producing a target protein, which method comprises expressing said protein in a host cell which contains a nucleic acid molecule which encodes a chimeric protein, said chimeric protein comprising a signal peptide from a bulk-secreted protein and said target protein, wherein said signal peptide is from a biological source taxonomically distinct from the host cell and wherein the chimeric protein does not include more than 15 residues of the signal peptide's native protein.

Previously described additional aspects of the invention and preferred embodiments thereof apply, mutatis mutandis, to this method.

By the term "taxonomically distinct" it is meant that the biological source of the host cell and that of the signal peptide are not from the same taxonomic class. Preferably not of the same taxonomic phylum.

"Taxonomic class" is defined as a taxonomic category of higher rank (i.e. more inclusive) than order but of lower rank (i.e. less inclusive) than phylum. Non-limiting examples of taxonomic class include Mammalia, Aves, Reptilia, Amphibia, Insecta, Arachnida, Scotobacteria, Anoxyphotobacteria, Magnoliids, Eudicotyledones, Monocotyledones, zygomycetes, and Basidiomycetes. For the purposes of this application the taxonomic grouping of Crustacea are considered a class.

"Taxonomic Phylum" is considered interchangeable with the term "taxonomic division" and is defined as a taxonomic category of higher rank (i.e. more inclusive) than class but of lower rank (i.e. less inclusive) than kingdom. Non-limiting examples of taxonomic phylum include Cordata, Echinodermata, Arthropoda, Annelida, Mollusa, Nematoda, Gracilicutes, Firmicutes, Bryophyta, Pterophyta, Anthophyta, Coniferophyta, Chlorophyta, Phaeophyta, Zygomycota, Ascomycota, Basidomycota, and Deuteromycota.

The 'signal peptide's native protein' is the protein whose secretion is naturally controlled by that signal peptide. Preferably no more than 10 residues, more preferably no more than 5 residues, most preferably none of the signal peptide's native protein is incorporated into the chimeric protein.

In a particularly preferred embodiment the invention provides a method of producing a target protein, which method comprises expressing said protein in a mammalian host cell which contains a nucleic acid molecule which encodes a chimeric protein, said chimeric protein comprising a signal peptide from a non-mammalian bulk-secreted protein and said target protein. Preferred are signal peptides from a copepod or an ostracod, e.g. *Gaussia princess* or *Vargula hilgendorfii*. Particularly preferred are the signal peptides from *Gaussia* or *Vargula luciferase* and most particularly the signal peptide from *Gaussia luciferase*.

Recent work has also shown that the untranslated region downstream of the coding region in an mRNA (the 3' untranslated region, 3'UTR) is also involved in the targeting of the mRNA to its correct intracellular compartment (Partridge 1999 et al). This ensures that translation occurs in the correct compartment and thus the resulting protein is in the correct compartment. When the 3'UTR of the transcript of a secreted protein is replaced by the 3'UTR of an intracellular protein the level of targeting of this transcript to membrane bound polysomes and eventual secretion of the protein is reduced. Addition of a signal sequence and 3'UTR from a secreted protein to the coding region of a normally intracellular protein directs this recombinant transcript to membrane bound polysomes and thus results in secretion of the normally intracellular protein.

Thus, it is envisaged that the nucleic acid molecule from which the chimeric protein of the invention is expressed will optionally also include a 3'UTR from a secreted protein, preferably a bulk-secreted protein, and most preferably the 3'UTR from *Gaussia luciferase* (or functionally active fragments or derivatives thereof). Further, if the target protein is normally an intracellular protein, the nucleic acid molecule encoding the target protein will be devoid of the native 3'UTR and optionally include a 3'UTR from a secreted protein, preferably a bulk-secreted protein.

BRIEF DESCRIPTION OF THE DRAWINGS

The invention will be further described with reference to the following non-limiting Examples in which:

FIG. 1. Shows the sequences of the signal peptides of Gaussia luciferase (SED ID NO:1), Chymotrypsin(ogen) (SEQ ID NO:5), Trypsin(ogen) 2 (SEQ ID NO:6), trypsin (ogen) A (SEQ ID NO:7), Amylase (SEQ ID NO:8) and Vargula luciferase (SEQ ID NO:2).

REFERENCES

Figure 2:
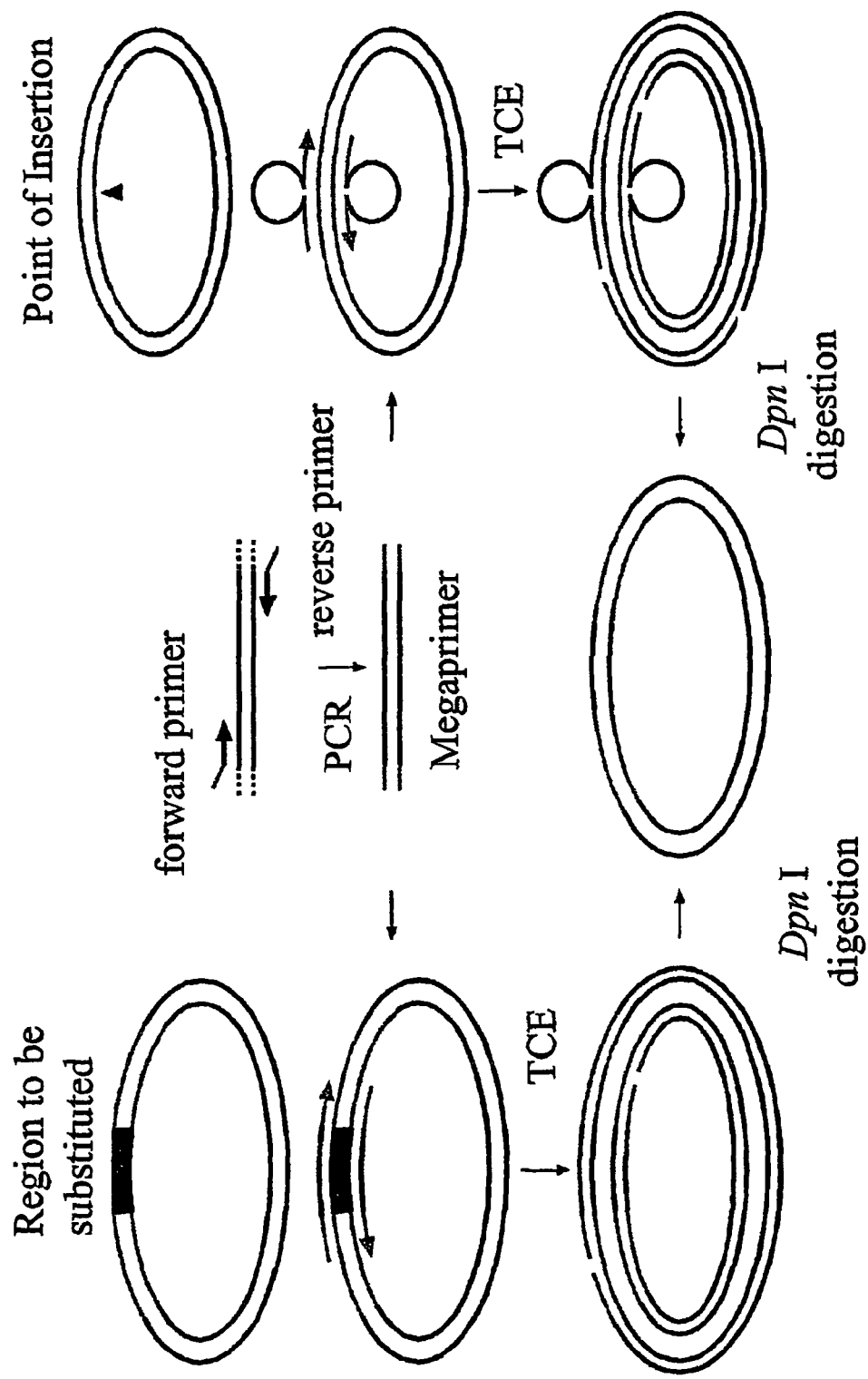
FIG. 2. Shows a simplified diagram showing the technique of seamless cloning.

Blobel and Dobberstein, (1975) J. Cell. Biol. 67: 835-851.
Görlich, D. and Rapoport, T. A. (1993) Cell 75:615-630.
Hesketh, J. E. (1996) Biochem Soc Trans vol. 24, no. 2, 1996, pages 521-527.
Kim, Y-J et al (1996) BIOCHEM. AND BIOPHYS. RES. COMMUNICATIONS, vol. 228, 1996, pages 324-327,
Martoglio, B and Dobberstein, B. (1998). Trends Cell Biol. 8: 410-415
Maltseva, E. L., Palmina, N. P. and Pryme, I. F. (1991b). Mol. Cell. Biochem. 106:49-54.
Partridge, K et al. (1999) Cytotechnology 30: 37-47
Pryme, I. F. (1988). Biochem. Biophys. Acta 967:218-223.
Pryme, I. F. (1989a). Mol. Cell Biochm. 87:93-103.
Pryme, I. F. (1989b). Int. J. Biochem. 21:119-125.
Pryme, I. F. and Hesketh, J. E. (1987). Cell Biol. Int. Repts. 11:615-623.
von Heijne, G (1990). J. Membr. Biol. 115:195-201.
von Heijne, G. (2002). (R. E. Dalbey and G. von Heijne, eds.) pp. 35-46, Academic Press.

EXAMPLES

Example 1

General Materials and Methods

Cultivation of CHO Cells

Stock cultures of the CHO cells (CHO AA8 Tet-Off and CHO K1 Tet-On) were grown in monolayer in the suitable medium, in 25 $cm^2$ or 75 $cm^2$ cell culture flasks. The cells were incubated in a humidified atmosphere of 5% $CO_2$ at 37° C. The seeding density was ~2.0×$10^4$ cells/$cm^2$, allowing the cells to reach 90-100% confluency within 2-3 days, meaning that the cultures had to be split every second or third day. Splitting was done by removing the medium from the flask and washing the cells twice with 1×PBS, before ~1.5 ml Trypsin-EDTA solution was added. After a short incubation (2-3 minutes) at 37° C., the flask was inspected under the microscope, to check that all cells had detached from the growth surface, before ~10 ml growth medium was added to the flask. Cells were then seeded out in flasks for further cultivation. If cells were to be used for transfection they were seeded out on 6-well plates.

Transfection of Cells and Preparation of Stable Populations 6.0×$10^5$ cells were plated out in each well on 6-well plates with medium (to a total volume of 2 ml per well). This gave suitable conditions for transfection (90-100% confluency) after 24 hours. The medium was then removed, and the cells were washed once with 1×PBS. The transfection mixture was made on a 96-well plate by adding 4 mg DNA to 150 ml medium in one well, and 10 ml Lipofectamine 2000 to 150 ml medium in another. The medium used was pure aMEM or DMEM (depending on the cells that were to be transfected) without any additives. After a 5 minute incubation at RT, the solution containing the DNA was added to the solution containing Lipofectamine, and these were mixed gently, before being incubated at RT for 20-30 minutes in order to allow the DNA and the Lipofectamine to form complexes. The transfection mixture (~320 ml) was then dripped gently on to the washed cells, before 500 ml pure medium (aMEM or DMEM with no additives) was added to each well and the cells were incubated for 6 hours. Medium containing excess DNA and Lipofectamine was removed and cells were washed twice with 1×PBS, before 2 ml full growth medium was added, and cells were further cultivated. Cells that were to be transiently transfected were cultivated for 24 hours before harvest of samples. Cells that were to become stable populations containing the plasmid construct with which they had been transfected, were cultivated as normal for 24 hours. For the next 20 days these cells were cultivated in a medium containing 400 mg/ml hygromycin. Transfected cells would be resistant to this antibiotic as the vector used contained the Hygr-gene. After these first 20 days of selection, the amount of hygromycin in the medium was kept at 200 mg/ml, in order to maintain the cells stably transfected. Every third week, the culture was transferred into a fresh flask, to avoid complete degradation of the proteins coating the growth surface, due to repetitive trypsinisation.

Recombinant Protein Expression

CHO AA8 Tet-Off cells were used for transient transfections. When transfected with a plasmid construct based on the pTRE2hyg-vector, these cells expressed the gene inserted into the plasmid's MCS constitutively. CHO K1 Tet-On cells were used for preparation of stably transfected cell populations. These cells were chosen because they could not express the gene inserted into the pTRE2hyg vector when grown in regular medium, and would therefore not be exhausted by recombinant protein synthesis during the selection process. Induction of recombinant protein expression was performed by addition of doxycycline to the growth medium. A suitable number of cells (2.5×$10^5$) in 2 ml growth medium were transferred to each well on 6-well plates and allowed to grow for 24 hours. The growth medium was then replaced with medium containing 1 mg/ml doxycycline, and cells were cultivated for 24 hours before harvest of sample. (For details on the Tet-Off and Tet-On expression system, see "User Manual PT3001-1", available on www.clontech.com).

Electrophoresis of DNA

Agarose gel electrophoresis was used for the separation of products of restriction endonuclease digestion, and for the determination of concentration of both PCR products and products of DNA purification procedures.

The prepared gel solution was poured into a gel chamber and allowed to cool and polymerize for 15-30 minutes at RT, before it was moved to an electrophoresis tray, prefilled with 1×TAE buffer. After loading the samples, electrophoresis was carried out at 60-100V for 40-90 minutes, until the first colour front of the loading buffer had migrated through ⅔ of the gel.

The fragments of the samples were visualized by UV-light and pictures were saved using the computer program Gel-Doc Multi-Analyst (version 1.1).

Extraction of DNA from Agarose Gels

For the purpose of extracting synthesized megaprimers for seamless cloning, and products of restriction enzyme digestion, QIAGEN MinElute Gel Extraction Kit was used, and the procedure was performed according to QIAGEN MinElute Handbook 10/2000, with an additional step in the end: The elution step was repeated, so that the final volume was ~20 µl. This protocol was used for extraction of DNA from both regular agarose (type I) and NuSieve agarose.

For the purpose of extracting synthesized probes for Northern blot analysis, GenElute Agarose spin column from Sigma was used, and the procedure was carried out according to the kit's product information.

Ligation

For this purpose Rapid DNA Ligation Kit from Roche was used, and the procedure was performed according to the Kit folder (version 1, November 1999)

For samples where the concentration of the DNA fragment that was to be inserted into the vector was very low (<20 ng/µl), all volumes were doubled, so that the final volume of the ligation mix was 20 µl instead of 10 µl.

3 µl of ligation mixture was used for the transformation of chemically competent ("heat-shock competent") *E. coli* DH5a cells.

Estimation of DNA Concentration by Agarose Gel Electrophoresis

The DNA sample that was to be measured, was run on an agarose gel in lanes next to a standard (a plasmid DNA or DNA fragment sample of known concentration), and the bands were visualized by exposing the gel to UV-light.

Bands of the unknown sample were then compared to the bands of the standard, and the DNA concentration of the unknown sample was estimated.

Estimation of DNA Concentration by Measuring A260

The DNA sample's absorbance at 260 nm was measured, and the concentration was calculated based on the assumption that a solution containing 50 mg/ml DNA has an optical density of 1,000.

DNA Sequencing

General reaction mix for sequencing PCR:

| | |
|---|---|
| 3 µl | (300-600 ng DNA) Small scale purified plasmid (miniprep) |
| 1 µl | pTRE2 sequencing primer (2.5 mM) |
| 4 µl | Big Dye |
| 2 µl | dH2O |

Thermocycling for sequencing PCR:

| | |
|---|---|
| 1 cycle | 95° C. 5 minutes |
| | 95° C. 10 seconds |
| 25 cycles | 50° C. 5 seconds |
| | 60° C. 4 minutes |
| 1 cycle | 4° C. 8 minutes |

The General Seamless Cloning Strategy

All constructs in this study were made using the seamless cloning strategy. Seamless cloning is a restriction site-free cloning method, to substitute and insert PCR products into vectors. The method has been further optimized and also extended to include deletion. In FIG. 2 methodology is shown for making both substitutions and insertions. A pair of primers with "tails" was used in a PCR reaction, with a donor plasmid that contained the sequence of interest (template). This was done in order to make a large double-stranded megaprimer that contained the sequence of interest and had additional tails at both ends; which were complementary to the sequences flanking the point of insertion/substitution on recipient plasmid.

General reaction mix for megaprimer synthesis, PCR:

| | |
|---|---|
| 100 ng | Template (donor plasmid) |
| 2.5 µl | Primer forward (10 µM) |
| 2.5 µl | Primer reverse (10 µM) |
| 1 µl | dNTPs (10 mM each) |
| 5 µl | Expand High Fidelity PCR Buffer |
| 0.75 µl | Expand High Fidelity polymerase (3.5 U/µl) | dH$_2$O to 50 ml

General thermocycling for megaprimer synthesis

| | |
|---|---|
| 1 cycle | 95° 5 minutes |
| | 95° C. 30 seconds |
| 25 cycles | Gradient 1 minute (temperatures depending on primer Tm) |
| | 72° C. 1 minute (this step was only used in "difficult" reactions) |
| 1 cycle | 72° C. 10 minutes |
| 1 cycle | 4° C. ∞ |

The PCR product (megaprimer) was run on a 1% agarose gel (3% NuSieve gel, if the megaprimer was smaller than 300 bp), visualized, cut out, and purified using the Qiagen Gel Extraction Kit. Another gel was then run in order to estimate the concentration of the megaprimer obtained by gel extraction. In a subsequent TCE reaction, the tails on the denatured megaprimer annealed to the vector at the sequences flanking the point of insertion/substitution. By polymerase activity, the megaprimer was integrated into a newly produced vector.

General reaction mix for TCE reaction:

| | |
|---|---|
| 6-30 ng | Template (recipient plasmid) |
| 40-100 ng | Megaprimer (100 molar fold, relative to template) |
| 0.5 µl | dNTPs (10 mM each) |
| 3 µl | 10 × Pfu reaction buffer |
| 0.5 µl | Pfu turbo DNA polymerase (2.5 U/µl) | dH$_2$O to 30 ml

General thermocycling for TCE reaction

| | |
|---|---|
| 20 cycles | 95° C. 2 minutes |
| | Gradient 10 minutes (temperatures depending on primer Tm) |
| 1 cycle | 40° C. ∞ |

After the completion of the TCE reaction, 0.5 µl of DpnI (20 U/µl) was added to each tube, and incubation was performed at 37° C. for 2 hours. (DpnI recognizes and digests methylated and hemimethylated DNA. Both donor plasmids and hybrid plasmids in the TCE-mix were therefore substrates for DpnI, whereas the newly synthesized mutant DNA was not, and remained intact). The digested TCE-mix was then used to transform *E. coli* DH5a cells. Plasmids were purified from single colonies, and analyzed by agarose gel electrophoresis and subsequent sequencing.

Alternative Megaprimer Synthesis for Seamless Cloning

The sequence that was to be inserted or substituted into a target plasmid, was in most cases present in another available plasmid. This other plasmid was then used as template in megaprimer synthesis. However, this was not always the case and for some constructs alternative templates were used in the synthesis of megaprimers.

Use of Overlapping Primers

This method was used for synthesis of small megaprimers (<50 bp). Reaction mix was made as described earlier but no template was added. The two primers were designed to have overlapping and complementary 3' portions. During PCR these 3' portions annealed to each other, and each primer was extended by polymerase activity using the 5' portion of the other primer as a template (see FIG. 2 A). The PCR product was purified and used in a TCE.

Use of Overlapping Oligonucleotides Plus Primers

Reaction mix was made as described earlier, but instead of a plasmid, two overlapping oligonucleotides were added as template. These two oligos were designed to have overlapping and complementary 3' portions. During PCR these 3' portions annealed to each other, and each oligo was extended by polymerase activity using the 5' portion of the other oligo as a template. The primers were designed to have 3' portions identical to the 5' portion of one of the oligos. In this way, the 3' portion of the primers annealed only to the extended oligos, and the oligos were further extended by polymerase activity using the 5' portion of the primers as template. The PCR product was purified and used in a TCE.

Re-Cloning of Mutant Plasmids

Re-cloning was done by firstly cutting both the "fresh" vector (pTRE2hyg) and the isolated mutant plasmid with the same restriction enzymes (BamHI and EcoRV). Cut mix for cutting out the sequence of interest:

| | |
|---|---|
| 25 μl | Mutant plasmid (100-200 ng/μl) |
| 1 μl | BamHI (20000 U/ml) |
| 1 μl | EcoRV (20000 U/ml) |
| 10 μl | 10 × Multicore buffer |
| 0.5 μl | 100 × BSA | dH$_2$O to 50 ml

Cut mix for the "fresh" vector (pTRE2hyg):

| | |
|---|---|
| 0.5 μl | pTRE2hyg (2 μg/μl) |
| 1 μl | BamHI (20000 U/ml) |
| 1 μl | EcoRV (20000 U/ml) |
| 10 μl | 10 × Multicore buffer |
| 0.5 μl | 100 × BSA | dH$_2$O to 50 ml

For cutting, these mixes were incubated at 37° C. for 2-3 hours.

The digested plasmids were then run on an agarose gel, and the DNA fragments of interest were purified using the Qiagen Gel Extraction Kit. A second gel was then run in order to estimate the concentration of the opened vector and the mutated fragment, yielded by gel extraction. The mutant fragment was ligated into the opened vector, using the Rapid DNA Ligation Kit from Roche.

The ligation mix was then used to transform E. coli DH5a cells, and colonies were screened for the correct ligation by small scale plasmid isolation and subsequent redigestion with BamHI and EcoRV.

Cut mix for screening ligation products:

| | |
|---|---|
| 5 μl | Isolated plasmid (100-200 ng/μl) |
| 0.5 μl | BamHI (20000 U/ml) |
| 0.5 μl | EcoRV (20000 U/ml) |
| 2 μl | 10 × Multicore buffer |
| 0.2 μl | 100 × BSA | dH$_2$O to 20 ml

The digested plasmids were then run on an agarose gel, and plasmids that seemed to have been correctly ligated were sequenced in the region of interest. Correct plasmids were then produced in large scale, by transferring the remains of the miniprep culture containing this plasmid, to a large volume of growth medium, and performing megaprep.

Work with Bacteria

Preparation of "Heat Shock" Competent Cells

A single colony of E. coli DH5a cells was inoculated in 5 ml LB medium, and incubated at 37° C. with shaking o/n. This culture was transferred to 500 ml LB-medium containing MgSO$_4$ at a concentration of 20 mM, and grown further for 2-4 hours (until OD$_{590}$ was between 0.4 and 0.6). This large culture was divided into two 250 ml GSA tubes, and bacteria were harvested by centrifugation at 4070 rcf (5000 rpm for GSA rotor) for 5 minutes at 4° C. After the media was removed, the pellets in the two tubes were each resuspended in 100 ml precooled TFBI, and incubated on ice for 5 minutes. Then the tubes were centrifuged, again at 4070 rcf for 5 minutes at 4° C., before the pellets were resuspended in 10 ml TFBII, and incubated on ice for 15-60 minutes. These suspensions were then aliquoted to precooled 1.5 ml tubes (100 ml to each tube) and immediately frozen at −80° C.

Transformation of Bacteria by "Heat-Shock"-Treatment 10 ml product of a TCE or 3 ml product of a ligation reaction, was added to 100 ml chemically competent ("heat-shock competent") E. coli DH5a cells (thawed on ice), and was incubated on ice for 30 minutes. The tube, containing plasmid and bacteria cells, was then incubated at 42° C. (water bath) for 90 seconds, and immediately cooled on ice, for 1-2 minutes. 1 ml SOC-medium was added to the tube, and the suspension was incubated at 37° C. for 45 minutes with shaking to avoid sedimentation. 50 ml of the suspension was plated out on a LB-plate containing 100 μg/μl ampicillin, (in this study all plasmids used for transformation contained a gene giving ampicillin-resistance). The rest of the suspension was centrifuged for 1 minute at 12000 rcf (13400 rpm in an Eppendorf minispin centrifuge), and the pellet was plated out on another LB-plate containing ampicillin. (In suspensions where the concentration of plasmid/product of ligation was expected to be very low, e.g. product of a TCE-reaction, only the pellet was plated out). Plates were then incubated at 37° C. o/n.

Small Scale Plasmid Preparation from E. coli ("Miniprep")

A single bacteria colony was inoculated in 5 ml LB-medium with 100 μg/μl ampicillin in a 15 ml tube, and incubated at 37° C. with shaking o/n. 1 ml of the culture was then transferred to a 1.5 ml tube and centrifuged at 18500 rcf (13200 rpm in an eppendorf 5417 centrifuge) for 1 minute. The supernatant was carefully poured out, and another ml of culture was added to the same tube, before it was centrifuged again for 1 minute. The supernatant was poured out, and 100 ml of solution I, containing 25 mg/ml RNaseA was added to the tube. The pellet was resuspended by vortexing. 200 ml of solution II was then added, and the tube was inverted 4-6 times, before it was incubated at RT for 3 minutes. 150 ml of solution III was added and the tube was mixed again by inversion (4-6 times). The tube was then incubated at RT for 10 minutes, before it was centrifuged at 18500 rcf for 5 minutes. 400 ml of the supernatant was transferred to a fresh 1.5 ml tube, 900 ml 96% EtOH was added, and the tube was centrifuged at 18500 rcf for 30 minutes. The EtOH was then poured out, and the pellet was washed by adding 150 ml 70% EtOH, and centrifuged at 18500 rcf for 2 minutes. The EtOH was removed using a vacuum pump, and the pellet was then dried in open air at RT. The pellet was finally resuspended in 50 ml TE-thin buffer, containing 25 mg/ml RNaseA. The yield of plasmid by this procedure was usually 5-10 µg (100-200 ng/µl).

Large Scale Plasmid Preparation from *E. coli* ("Megaprep")

For this purpose QIAGEN Plasmid Mega Kit was used, and the procedure was performed according to QIAGEN Plasmid Purification Handbook 09/2000. The yield of plasmid by this procedure was usually 1-4 mg (1-4 µg/µl).

Harvesting Samples for Luciferase Measurement

Harvesting Medium Samples

Figure 3:
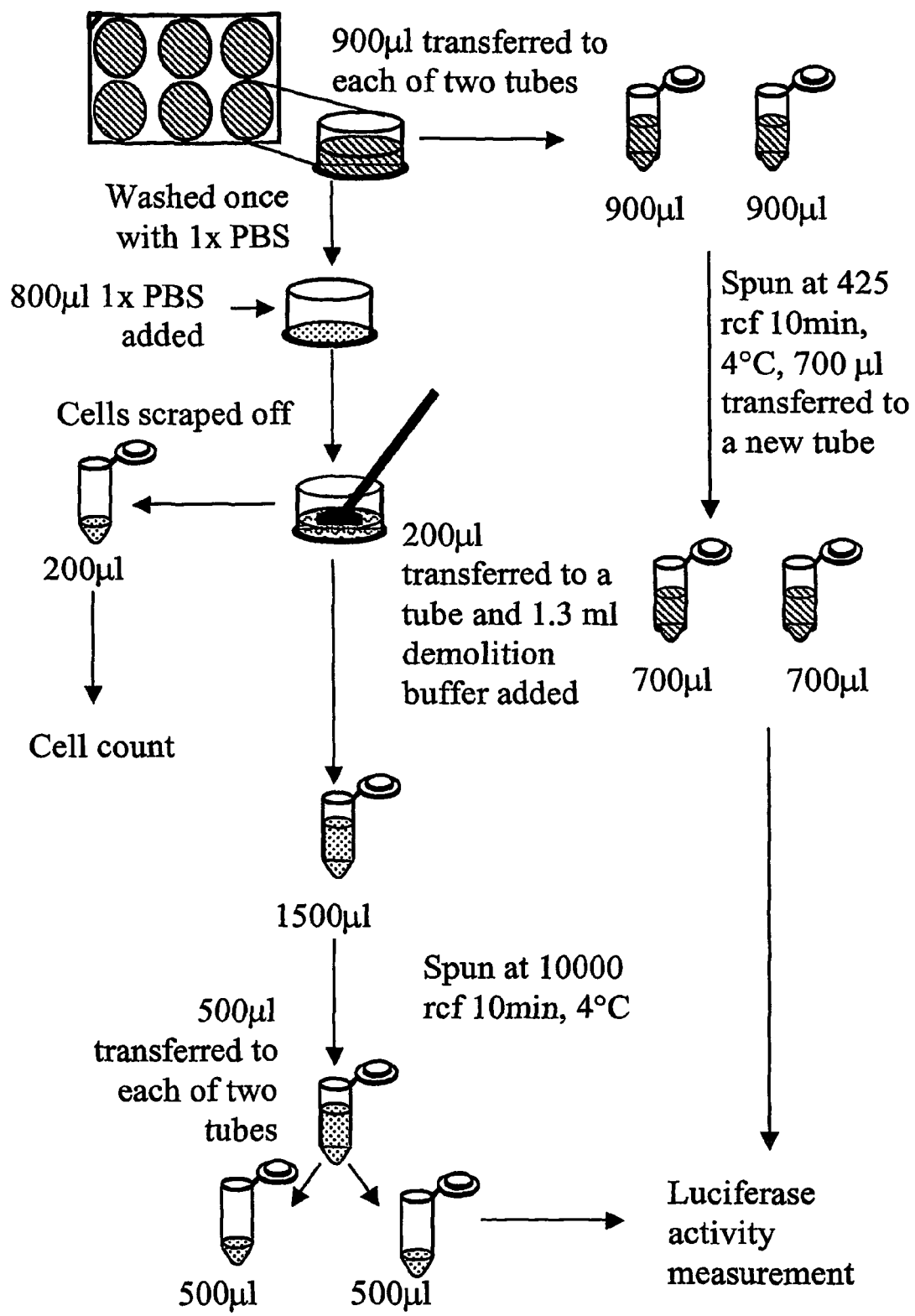
FIG. 3. Shows a schematic overview of the methodology involved in the preparation of extracts for *luciferase* assay.

The medium in the well was removed and divided into two 1.5 ml tubes. (Due to evaporation, only 1800 µl of the original 2000 µl medium was left in the well after 24 hours, so 900 µl was transferred to each of the two tubes). These tubes were centrifuged at 425 rcf for 10 minutes, at 4° C., before the top 700 µl was transferred to fresh tubes (this was done to remove dead cells present in the medium sample). One of the tubes was to be used for measurement of luciferase activity, while the other served as a backup sample (see FIG. 3).

Harvesting Cell Samples

After the medium was removed, and treated as described above, the well was washed once with 1×PBS, before 800 µl 1×PBS was added. The cells were then scraped off the growth surface very gently, with a cell lifter, and mixed gently with a pipette, in order to get a homogenous cell-suspension. 200 µl of this suspension was transferred to each of two 1.5 ml tubes; one of which was immediately used to count the number of cells on a Nucleocounter from Chemometec. The other tube was added 1300 µl lysis buffer and incubated at RT for 5 minutes, during which the contents were mixed a couple of times by inverting the tube. The cell debris was removed by centrifugation at 10000 rcf for 10 minutes at 4° C. 500 µl of the supernatant was transferred to each of two fresh 1.5 ml tubes. As for the medium, one of the tubes was to be used for measurement of luciferase activity, while the other served as a backup sample (see FIG. 3). Both medium and cell samples were frozen at −80° C., until the time of activity measurements.

Measurement of Luciferase Activity

Luciferase activity was measured using a Lucy 1 (Anthos) luminometer. All samples were taken out from −80° C., and thawed on ice. Each sample was added Renilla buffer to a suitable dilution (determined by a pre performed dilution assay) and 10 µl of this dilution was transferred to each of two wells on a white 96-well plate, (two parallels were always measured for the same sample).

| | |
|---|---|
| Sample volume | 10 µl |
| Substrate volume dispensed | 150 µl |
| Lag time | 1.67 seconds |
| Integration time | 1 second |
| Detector filter | Empty |

The raw data obtained from the luminometer was corrected for the different dilutions made and for the volumes of the original samples. The measurement data was also corrected for number of cells in the well from which the sample was taken For each sample the results could thereby be presented as total luciferase activity per cell in the medium and in the cell extract of the well from which the sample had been taken.

Example 2

Figure 4:
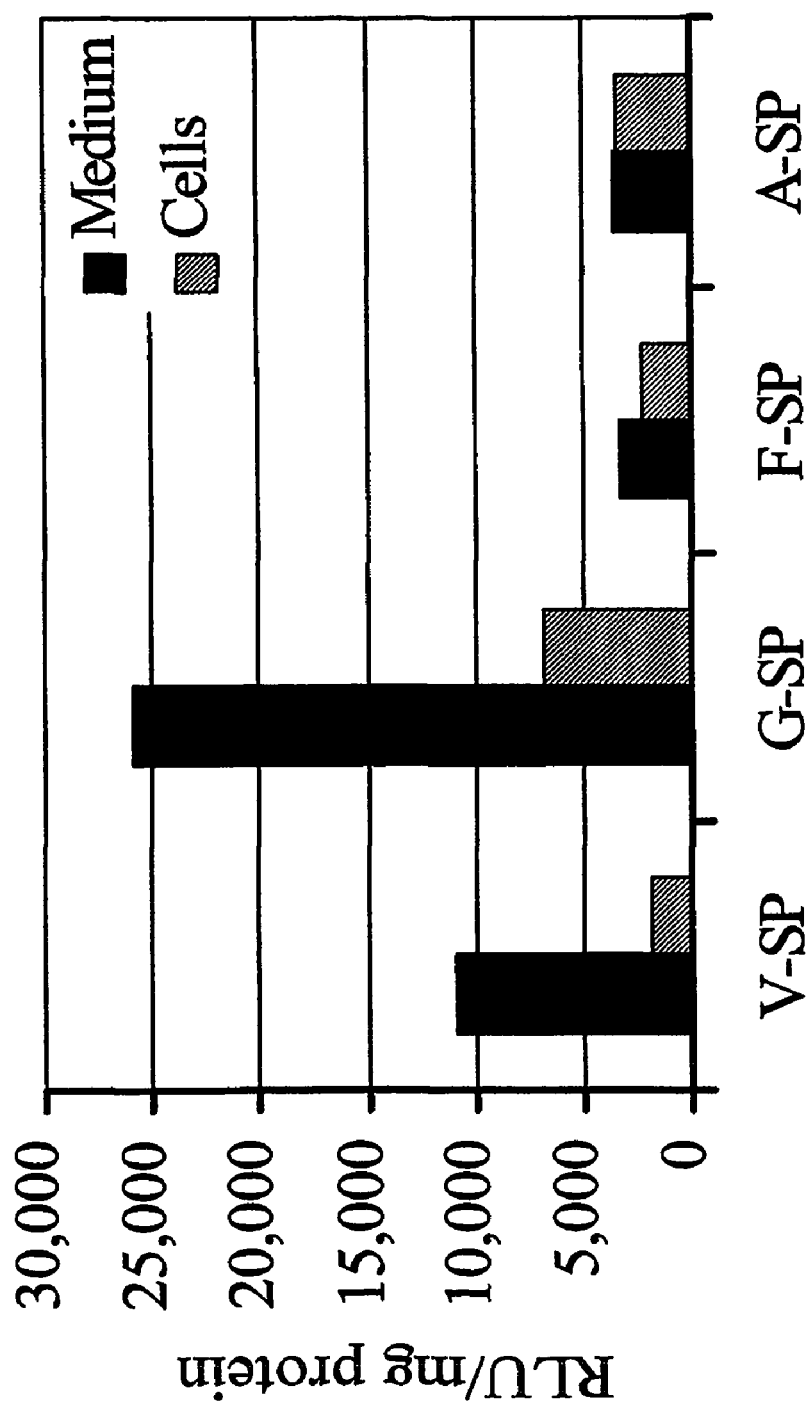
FIG. 4. Shows the effect of different signal peptides on the secretion of *Vargula luciferase*.

Experiments were undertaken to assess the efficiency by which different signal peptides could augment the secretion of *Vargula luciferase*. Signal peptides from *Vargula luciferase*, *Gaussia Luciferase*, *Human follistatin*, and *Human albumin* were operably linked to the coding region of *Vargula luciferase* as described above. Levels of luciferase, as measured by relative light units per mg of protein, were determined for both the cells and the medium. As can be seen from FIG. 4 both *Vargula* and *Gaussia luciferase* signal peptides were capable of promoting efficient secretion of *Vargula luciferase*. The *Gaussia* signal peptide was particularly effective in the total level of reporter protein secreted however the ratio of secreted/non-secreted is similar to that observed with the *Vargula luciferase* signal peptide.

The secretion of *Vargula luciferase* induced by the folistatin or albumin signal peptide is lower than that induced by the reporter protein's native signal peptide. Follistatin and albumin are secreted proteins but neither are bulk-secreted proteins. This shows that the signal peptide of the invention must be derived from a bulk-secreted protein.

Example 3

Figure 5:
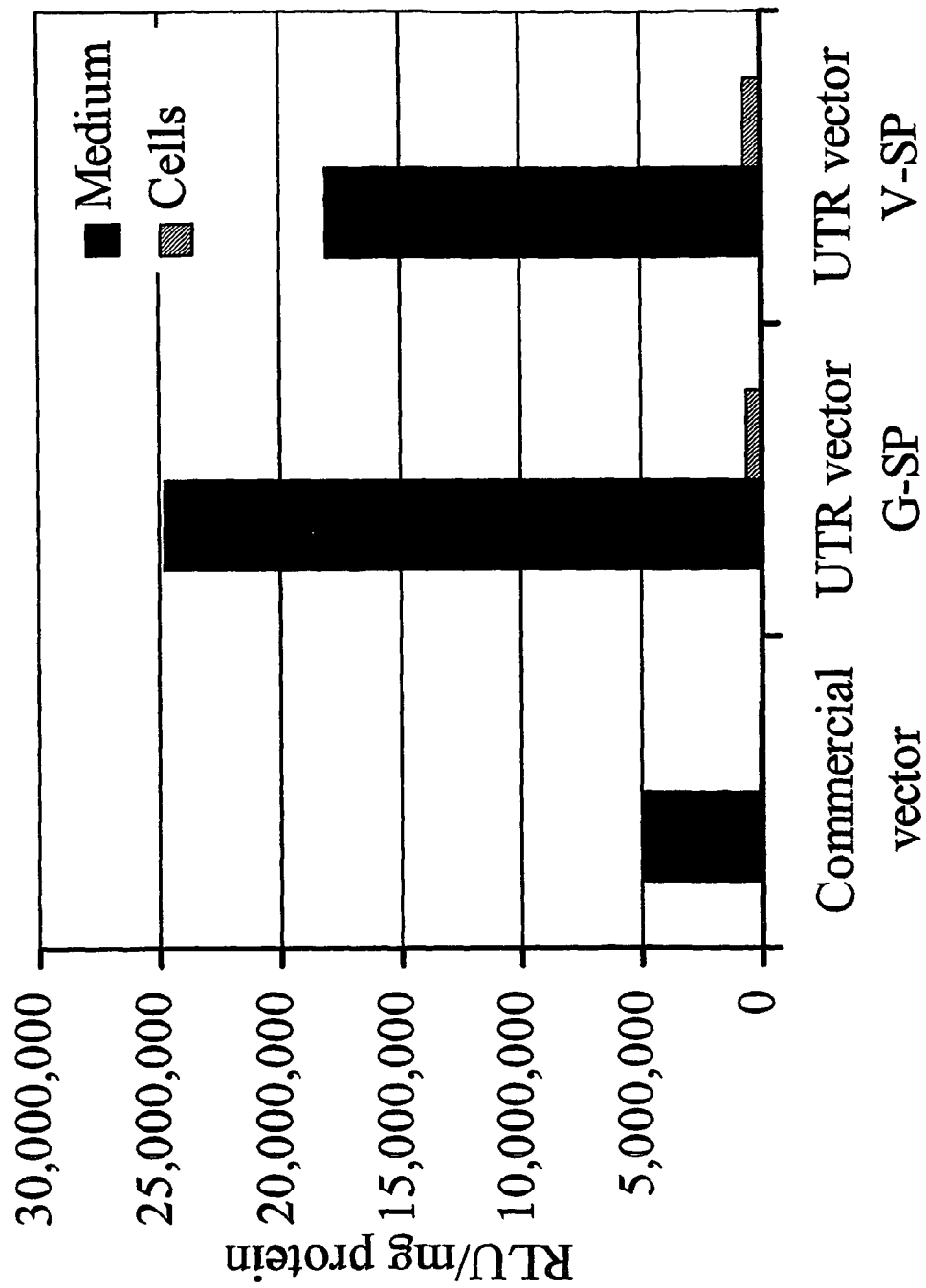
FIG. 5. Shows the effect of different signal peptides on the secretion of *Gaussia luciferase*.

Experiments were undertaken to assess the efficiency by which different signal peptides could augment the secretion of *Gaussia luciferase*. Signal peptides from *Vargula luciferase*, and *Gaussia Luciferase* were operably linked to the coding region of *Vargula luciferase* as described above. Also used was a commercial secretion vector (Invitrogen, pSecTag/Hygro A, B, C, cat no. V910-20). This vector uses the murine Igκ chain signal peptide to induce secretion of the heterologous protein. Levels of luciferase, as measured by relative light units per mg of protein, were determined for both the cells and the medium. As can be seen from FIG. 5 both *Vargula* and *Gaussia luciferase* signal peptides were capable of promoting efficient secretion of *Gaussia luciferase*. The *Gaussia* signal peptide was particularly effective in the total level of reporter protein secreted however the ratio of secreted/non-secreted is similar to that observed with the *Vargula luciferase* signal peptide.

The secretion of *Vargula luciferase* induced by the murine Igκ chain signal peptide is more than 5 times lower than that induced by the reporter protein's native signal peptide. Again the use of a signal peptide from a bulk-secreted protein is superior to that of a signal peptide from a protein whose secretion is controlled at the level of expression.

Example 4

Figure 6:
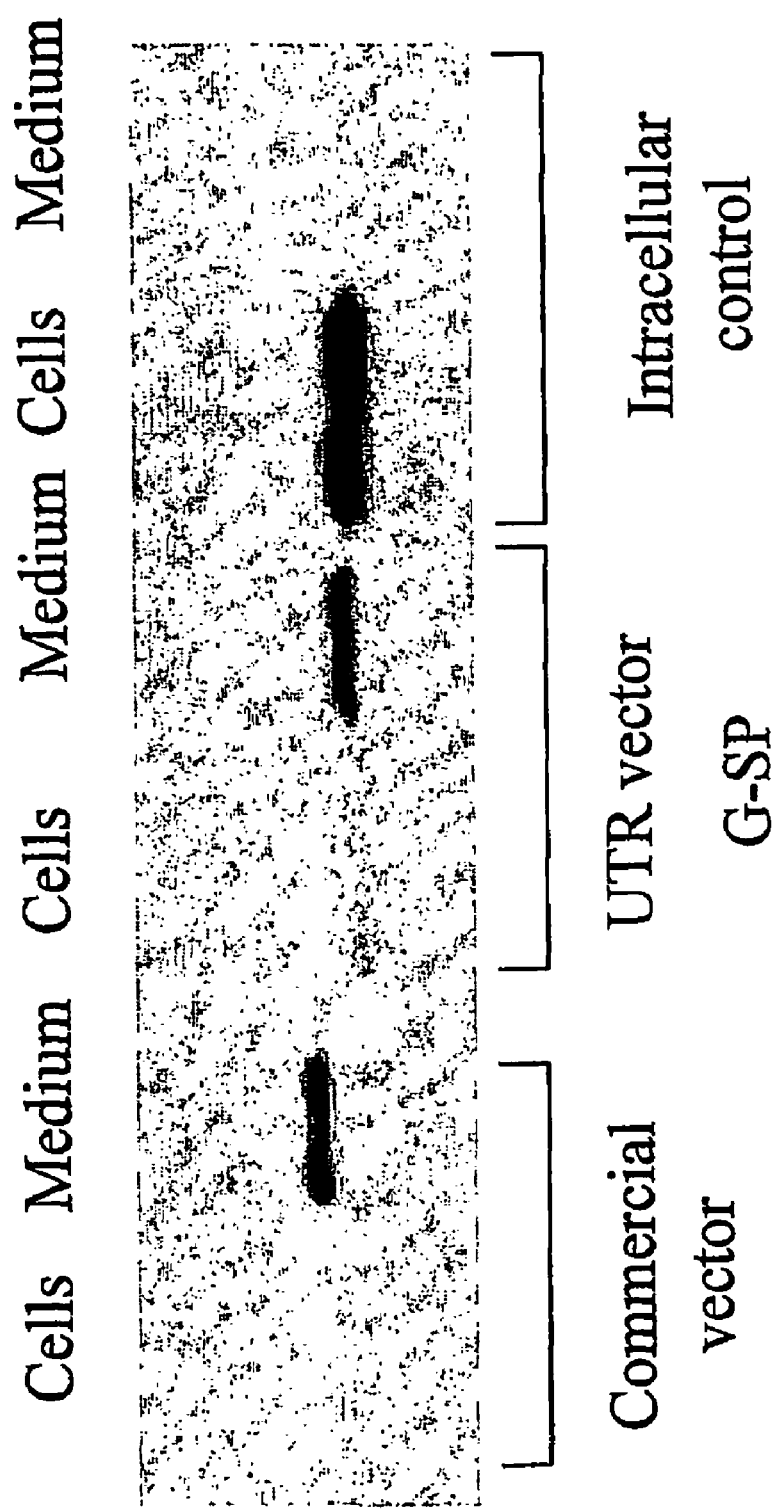
FIG. 6. Shows Western detection of EGFP showing the effect of different signal peptides on its secretion and the effect of seamless cloning on the size of the expression product.

The ability of *Gaussia luciferase* signal peptide to induce the secretion of a naturally non-secreted protein was compared to the ability of murine Igκ chain signal peptide. CHO cells were transfected with vectors in which the coding sequence for EGFP was operably linked to the above signal peptides. Protein was extracted from both cells and the medium, normalized for variations in protein concentration, and subjected to Western detection As can be seen from FIG. 6 the *Gaussia luciferase* signal peptide is more efficient at inducing the secretion of EGFP when compared to murine Igκ chain signal peptide. These results also show that the use of seamless cloning techniques results in a protein product of a size more similar to that of the intracellular protein.

Example 5

Signal peptides from *Gaussia luciferase*, trypsin(ogen)-2 and chymotrypsin(ogen) were operably linked to the coding region of *Gaussia luciferase* and expressed in CHO cells. Luciferase activity, measured by relative light units per cell was monitored both in the medium and in cell extracts after 24 hours incubation.

Figure 7:
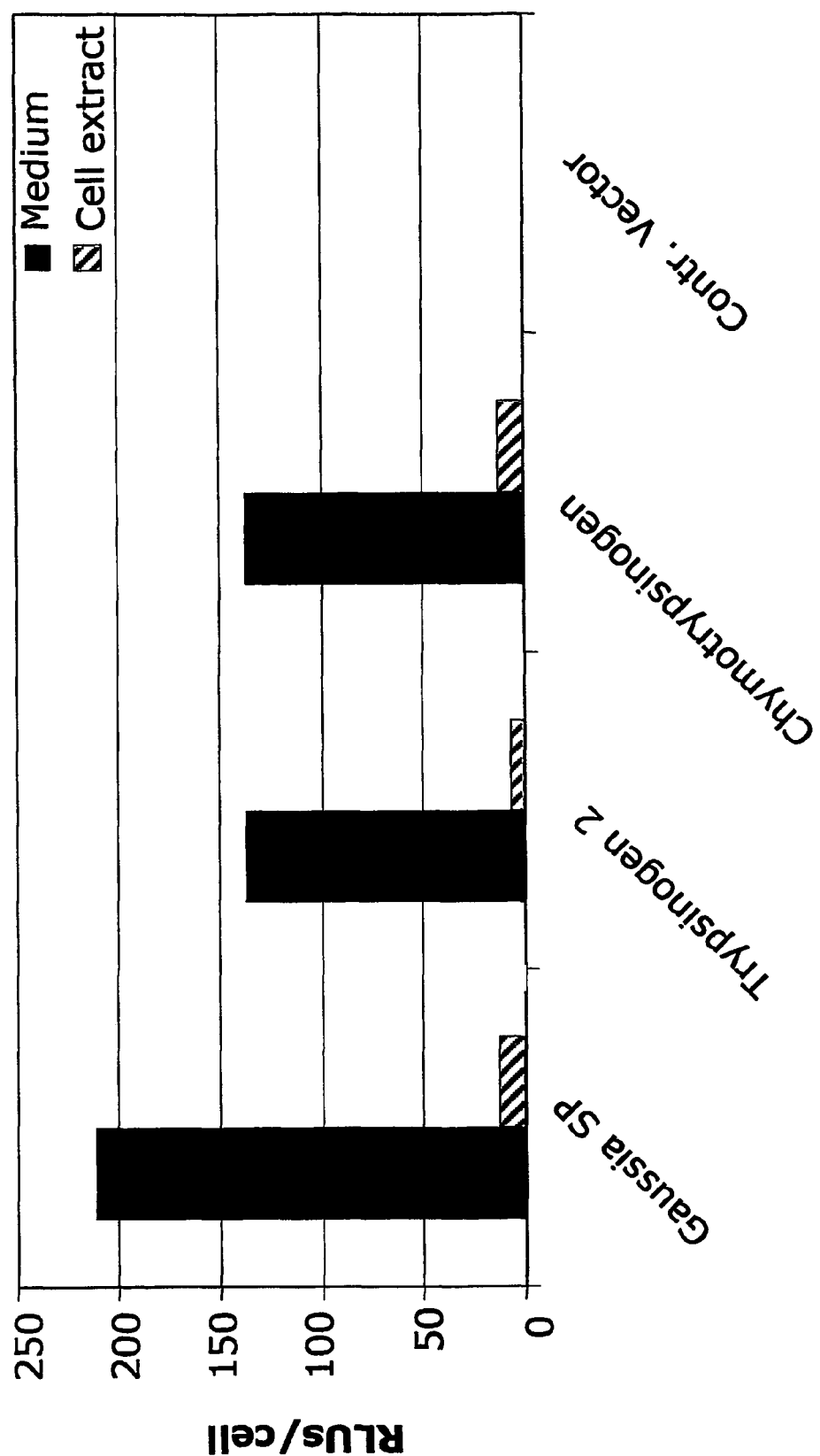
FIG. 7. Shows the effect of different signal peptides on the secretion of *Gaussia luciferase*.

As can be seen in FIG. 7 the *Gaussia* signal peptide is superior to both trypsin(ogen)-2 and chymotrypsin(ogen) signal peptides with respect to promoting secretion of the reporter protein. When chymotrypsin(ogen) and trypsin (ogen)-2 (examples of mammalian bulk-secreted proteins) signal peptides were used, levels of secretion of recombinant protein were reduced by about 37% when compared to the *Gaussia* signal peptide.

These data show that signal peptides from non-mammalian bulk-secreted proteins are superior to signal peptides from mammalian bulk-secreted protein when inducing production/secretion of recombinant proteins in non-mammalian cells.

Example 6

Signal peptides derived from *Gaussia luciferase*, human interleukin-2 and human albumin and the complete human albumin pre-pro sequence were operably linked to the coding region of *Gaussia luciferase* and expressed in CHO cells. Luciferase activity, measured by relative light units per cell, was monitored both in the medium and in cell extracts after 24 hours incubation. The pre-pro sequence comprises the signal peptide (pre) and the sequence of amino acids cleaved off proalbumin during its transit through the Golgi apparatus which yields mature, active albumin (pro).

Figure 8:
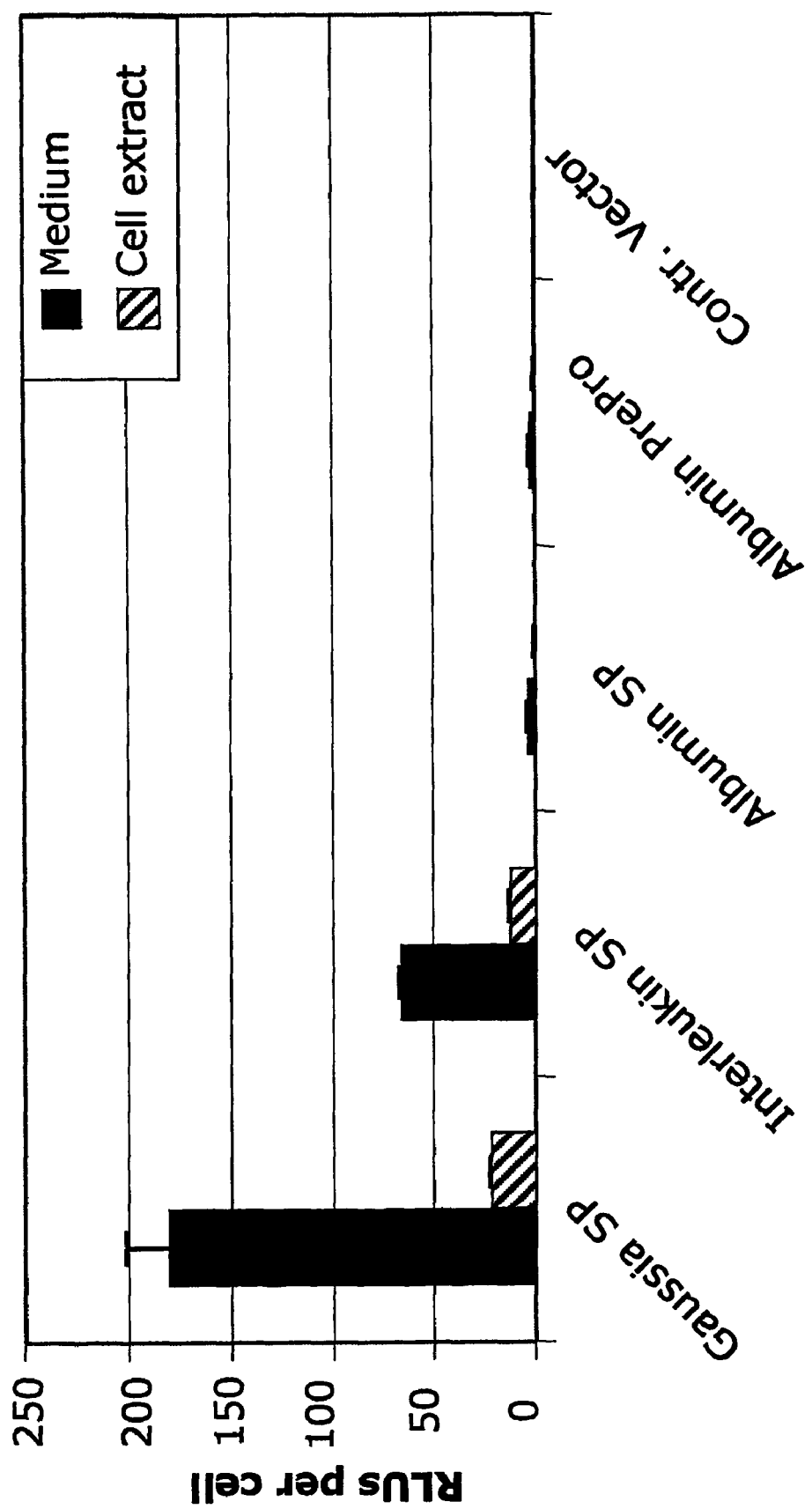
FIG. 8. Shows the effect of different signal peptides and the pro sequence of albumin on the secretion of *Gaussia luciferase*.

As can be seen from FIG. 8, the signal peptide from *Gaussia luciferase* was more effective than the signal peptides of human interleukin-2 (example of a mammalian protein, the secretion of which is controlled at the level of gene expression) protein and albumin (example of mammalian protein which is constitutively secreted) with regard to recombinant protein production/secretion.

This data demonstrates that signal peptides from non-mammalian bulk secreted are particularly effective in inducing recombinant protein production and secretion from mammalian cells when compared with signal peptide from either constitutively secreted or mammalian proteins whose secretion is controlled at the level of gene expression.

The invention claimed is:

1. A method of producing a target protein, which method comprises expressing said protein in a host cell which contains a nucleic acid molecule which encodes a chimeric protein, said chimeric protein comprising
   (i) a signal peptide, wherein the signal peptide has a sequence selected from SEQ ID NO: 1 or SEQ ID NO: 2 or a derivative thereof having at least 70% sequence identity, and wherein said derivative retains the ability of said signal peptide to enhance or induce secretion of said target protein;
   (ii) said target protein, and
wherein the chimeric protein incorporates less than 15 amino acid residues of the native protein of the signal peptide.

2. The method of claim 1 wherein said host cell is a eukaryotic cell.

3. The method of claim 2 wherein the host cell is a mammalian cell.

4. The method of claim 1, wherein said chimeric protein does not incorporate the native protein of the signal peptide.

5. The method of claim 1, wherein the signal peptide comprises the amino acid sequence set forth in SEQ ID NO: 9.

6. The method of claim 1, wherein the target protein is not naturally secreted.

7. A method for obtaining a target protein from the media of a host cell culture comprising the host cell as recited in claim 1, which method comprises expressing protein from said host cells, harvesting the culture media of said cells and extracting and purifying said target protein therefrom.

8. The method of claim 1, wherein said host cell is from a biological source taxonomically distinct from *Gaussia princeps* or *Vargula hilgendorfii*.

9. The method of claim 1, wherein the derivative of SEQ ID NO: 1 or SEQ ID NO: 2 has at least 80% sequence identity.

10. The method of claim 1, wherein the derivative of SEQ ID NO: 1 or SEQ ID NO: 2 has at least 90% sequence identity.

* * * * *